United States Patent [19]
Cast et al.

[11] Patent Number: 6,001,656
[45] Date of Patent: Dec. 14, 1999

[54] METHOD FOR THE DETECTION OF CREATININE

[75] Inventors: Todd K. Cast; Michael J. Pugia, both of Granger, Ind.

[73] Assignee: Bayer Corporation, Elkhart, Ind.

[21] Appl. No.: 09/161,768

[22] Filed: Sep. 28, 1998

[51] Int. Cl.$^6$ .................................................. G01N 33/70
[52] U.S. Cl. .......................... 436/98; 436/106; 436/164; 436/169; 436/904; 422/55; 422/56
[58] Field of Search .............................. 436/98, 106, 111, 436/164, 169, 904; 422/55, 56

[56] References Cited

U.S. PATENT DOCUMENTS

| | | | |
|---|---|---|---|
| 5,173,431 | 12/1992 | Pugia et al. | 436/86 |
| 5,362,633 | 11/1994 | Pugia | 435/28 |
| 5,374,561 | 12/1994 | Pugia | 436/98 |
| 5,610,073 | 3/1997 | Chu et al. | 436/98 |
| 5,662,867 | 9/1997 | Pugia et al. | 422/56 |
| 5,733,787 | 3/1998 | Messenger et al. | 436/98 |

FOREIGN PATENT DOCUMENTS 043469  1/1982  European Pat. Off. .

OTHER PUBLICATIONS

Traylor et al, Tetrahedron, vol. 40, No. 3, pp. 553–568, 1984.

*Primary Examiner*—Maureen M. Wallenhorst
*Attorney, Agent, or Firm*—Jerome L. Jeffers

[57] ABSTRACT

Disclosed is an improvement to the assay for creatinine in fluid test samples by contacting the test sample with a reagent formulation containing cupric ions, a hydroperoxide and an oxidizable dye. The improvement involves the inclusion of one or more selected quinolines in the reagent formulation. When the quinoline is substituted with methyl in the 2–5 position and/or a methoxy in the 2–6 position auto-oxidation of the oxidizable dye is reduced. When the quinoline is further substituted in an otherwise unsubstituted carbon atom in the 2–8 position, the assay's resistance to interference from hemoglobin and ascorbate is increased.

6 Claims, No Drawings

METHOD FOR THE DETECTION OF CREATININE

BACKGROUND OF THE INVENTION

The present invention is an improvement to the method of detecting creatinine in samples of body fluid. There is disclosed in U.S. Pat. No. 5,374,561 a method for the detection of creatinine in urine which involves contacting a urine sample suspected of containing creatinine with cupric ions, a hydroperoxide and an oxidizable dye which provides a colored response in the presence of oxygen free radicals and a hydroperoxide. In this assay, the first step involves the formation of a $Cu^{++}$.creatinine chelated complex. The oxidizable dye is oxidized by the transfer of an electron therefrom to the $Cu^{++}$.creatinine complex to provide the non-reactive $Cu^{+}$.creatinine form which is regenerated to $Cu^{++}$.creatinine by the loss of an electron to the hydroperoxide. This assay works well in the absence of hemoglobin and ascorbate, but in the presence of hemoglobin and/or ascorbate, which are normally present in clinical urine samples, the precision of the assay is affected due to the tendency of hemoglobin and/or ascorbate to oxidize the dye which results in false positive results. In addition, the redox dye can auto-oxidize over time in the presence of copper ion thereby reducing the shelf life of this type of assay. Accordingly, it would be desirable and it is an object of the present invention to provide an improved reagent system for the detection of creatinine in a fluid test sample in which the tendency of hemoglobin and/or ascorbate in the test sample to cause falsely positive results and the auto-oxidation of the redox dye is reduced.

SUMMARY OF THE INVENTION

The present invention is an improvement to the method for the detection or determination of creatinine in a fluid test sample which involves contacting the test sample with cupric ions, a hydroperoxide and an oxidizable dye which provides a detectable colored response upon being oxidized when the cupric ions and creatinine combine to form a complex having peroxidase activity. This type of assay suffers from two drawbacks. First of all, the oxidizable dye can undergo auto-oxidation in the presence of transition state metals thereby shortening the assay reagents' shelf life. In addition, the presence of hemoglobin and/or ascorbate in the fluid test sample can cause false positive results due to their ability to oxidize the oxidizable dye in the absence of creatinine. It has now been discovered that these problems can be ameliorated by the addition of certain quinoline compounds to the assay reagents. Typically, those quinolines which have a methyl group in the 2–5 position and/or methoxy in the 2–6 position have been found to reduce or eliminate the problem of auto-oxidation. Certain quinoline compounds, i.e. those which have at least one nitro, amine, halogen or hydroxyl group in the 2–8 position and a methyl or methoxy group in position 2–6, have been found to have a positive effect on the problem of auto-oxidation and also to substantially reduce the tendency of hemoglobin and/or ascorbate to oxidize the dye thereby reducing the incidence of false positive results in the assay.

DESCRIPTION OF THE INVENTION

A novel method for the colorimetric determination of creatinine in fluid test samples is disclosed in U.S. Pat. No. 5,374,561. This method takes advantage of the peroxidase activity of creatinine/cupric ion metal complexes. In this assay, the chelation of cupric ions by creatinine produces a complex having peroxidase like activity which is capable of catalyzing the oxidation of an oxidizable dye such as tetramethyl benzidine by a hydroperoxide such as diisopropyl benzene dihydroperoxide to thereby provide a colored response. It has been discovered more recently that the accuracy of this assay is adversely affected by auto-oxidation of the oxidizable dye in the presence of metals which catalyze oxidation of redox indicators by an oxygen source through electron transfer, thereby reducing the reagent's shelf life. Of greater concern is the presence of hemoglobin and/or ascorbate in the test fluid which can oxidize the dye in the absence of creatinine resulting in false positive results.

Traylor et al discuss the capability of aromatic pyridines to increase peroxidase activity in Tetrahedron, 40:1984; 553-68. This teaching suggests that aromatic amines like quinoline cause redox dye oxidation in the presence of hemoglobin. In U.S. Pat. No. 3,853,472 to Rittersdorf there is disclosed a method for the detection of blood in urine which indicates that quinolines increase peroxidase activity as evidenced by increased redox dye oxidation.

It has now been discovered that certain quinoline compounds, rather than increasing peroxidase activity, can reduce the problems associated with auto-oxidation of the oxidizable dye. Those quinolines which are useful for this purpose are characterized by being substituted with methyl in the 2–5 position and/or methoxy in the 2–6 position. Thus, by adding one or more of these quinoline compounds to the reagent formulation at a concentration of from 10 to 300 mM, preferably from 50 to 150 mM, the shelf life of the reagent system can be extended.

Suitable quinolines for use in the present invention include those of the formula:

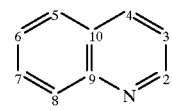

which are substituted with a methyl group at a carbon atom occupying position 2–5 of the molecule, a methoxy group at an otherwise unsubstituted carbon atom occupying position 2–6 of the molecule or both of the above.

Another, more limited class of quinolines can be added to the $Cu^{++}$.creatinine reagent system to control the adverse effects of hemoglobin and/or ascorbate on the oxidizable dye. These quinolines, which also have the effect of reducing the effects of auto-oxidation are characterized by at least one nitro, amine, halogen or hydroxyl group in the 2–8 position of the quinoline and a methyl in position 2–5 or methoxy group in position 2–6. They are typically added to the assay formulation in amounts as described above.

In the $copper^{++}$ assay the source of cupric ion may be any soluble copper salt whose anion does not detrimentally interact with the reaction for the colorimetric detection of creatinine. Suitable salts include copper sulfate, nitrate oxide, hydroxide, phosphate, iodide, chloride, bromide, acetate or oxalate. Other soluble cupric salts may be used provided that they allow formation of the CuII.Creatinine complex. Those salts whose anion binds too strongly to the copper will not allow the copperII.Creatinine complex to be formed. Accordingly, CuII complexes such as those formed between cupric ions and EDTA, HEDTA, EGTA and DTPA would not release sufficient CuII for formation of the CuII-.Creatinine complex. It has been observed that the citrate and sulfate salts have the lowest blank reactivity and, accordingly, they are preferred. Cupric citrate is particularly preferred due to its exhibiting the least blank reactivity and the greatest formation of the CuII.Creatinine complex. Salts which oxidize the dye in the absence of creatinine are less desirable. Salts such as cupric 2,2'-bipyridine can cause a significant oxidation of TMB in the absence of creatinine, and are, therefore, unsuitable for use in the present invention. When copper citrate is used as the cupric ion source, the concentration of citrate ion should be at least that of copper. An excess of citrate ion of at least twice that of the copper ion is preferred to ensure complete complexation of CuII by the citrate.

Typically, when urine is the aqueous fluid being tested, the concentration of cupric ion will be from 5 to 30 mM since the reference range of creatinine in urine is 3 to 20 mM. This range would vary in other fluids such as serum where one would preferably employ a concentration of cupric ion in the range of from 0.05 to 0.30 mM. The Cuprous ion tends to cause some background interference due to oxidation of the dye in the absence of creatinine. Accordingly, $Cu^+$ salts cannot be used.

Suitable oxidizable indicators include, for example, benzidine; o-tolidine; a 3,3',5,5'-tetraalkylbenzidine wherein the alkyl group includes from one to about six carbon atoms; o-dianisidine; 2,7-diaminofluorene; bis-(n-ethylquinol-2-one)-azine; (N-methylbenzthiazol-2-one)-(1-ethyl-3-phenyl-5-methyltriazol-2-one)-azine or combinations thereof.

Suitable hydroperoxides for use in the present invention include cumene hydroperoxide; 5-butyl hydroperoxide; diisopropylbenzene hydroperoxide; 1-hydroxycyclohexane-1-hydroperoxide; 2,5-dimethyl-hexane-2,5-dihydroperoxide; paramenthane hydroperoxide; 1,4-diisopropylbenzene monohydroperoxide; p-t-butyl-isopropylbenzene hydroperoxide; 2-(α-hydroperoxyisopropyl)-6-isopropylnaphthalene; tetralin hydroperoxide or combinations thereof.

Typically, the reagent system, comprising the soluble copper salt, hydroperoxide and oxidizable indicator will be dissolved in water. However, organic solvents can be incorporated into the system provided they do not interfere with the assay mechanism. The concentration of the hydroperoxide and oxidizable indicator will normally range from 10 to 150 mM with a range of from 60 to 100 mM being preferred.

In the practice of the invention, the assay can be performed in either the wet or the dry (test strip) format. In carrying out the assay, the test sample is mixed with the copper salt, e.g. cupric citrate, the dye and the hydroperoxide at a buffered pH, preferably from 4.0 to 9.0, through the use of a reagent strip or aqueous and acetonitrile solutions of reagents. Reagent strips are prepared in the conventional manner of dipping an absorbant carrier into an aqueous solution of the cupric salt and buffers, drying the carrier and then dipping it into an organic solution of the dye and hydroperoxide with subsequent drying.

The present invention is further illustrated by the following Examples:

EXAMPLE I

A creatinine reagent for use in this experiment was prepared by a two dip method in which a strip (⅓ inch ×⅓ inch) of Whatman cellulose filter paper grade 3 MM pad on a ⅓ inch by ½ inch polystyrene handle was dipped into a first dip solution with subsequent drying at 110° C. for 10 minutes followed by dipping it into a second dip solution and drying. The dip solutions were formulated as follows:

| Component | Concentration |
|---|---|
| 1st Dip | |
| CuSO4 | 30 mM |
| Citrate | 50 mM |
| Buffer: Glycerol-2-phosphate | 750 mM |
| Surfactant: Aerosol IB-45 | 1.5% |
| pH | 6.80 |
| Water | |
| 2nd Dip | |
| 3,3',5,5'-Tetramethylbenzidine (TMB) | 33 mM |
| Diisopropyl Benzene Dihydroperoxide (DBDH) | 80 mM |
| Polymer: Plasdone | 2.5% |
| Quinoline; 4-Hydroxy-2-methylquinoline | 100 mM |
| Ethyl Orange | 0.32% |
| Alcohol | |

This creatinine reagent demonstrates a large stability shift as shown in Table 1.

TABLE 1

The Stability Shift of the Creatinine Formula

| Storage Temperature | ND result for a 30 mg/dl sample observed within 3 months of storage |
|---|---|
| 25° C. | 21 |
| 30° C. | 23 |
| 40° C. | 24 |
| 50° C. | 19 |
| 60° C. | 18 |

A specimen containing either 30, 100 or 200 mg/dL of creatinine should read the expected result throughout the shelf life of the strip. However, in the stability shift demonstrated by Table 1, numerical designations as high as 24 were observed with a sample containing 30 mg/dL creatinine. This result is unacceptably high since visual results are measured by interpolation using a color chart with numerical designations of 10, 20 and 30 for the colors corresponding to 30, 100 and 200 mg/dL of creatinine concentration. For example, a result for a sample with 250 mg/dL should produce a numerical designation result of 25 or halfway between the results expected for samples containing 100 mg/dL and 200 mg/dL creatinine. As can be determined from Table 1, numerical designations (ND) as high as 24 were observed with a sample containing 30 mg/dL creatinine that should read as 10.

Several theories were pursued concerning the cause of the stability shift. By elimination of components, it was determined that the problem was related to auto-oxidation of the redox indicator, and it was discovered that when lepidine (4-methylquinoline) 100 mM was added to the creatinine formula, the visual stability of the assay improved dramatically as demonstrated by the date of Table 2.

TABLE 2

The Stability Shift of the Creatinine Formula with Lepidine

| Storage Temperature | ND result for a 30 mg/dl sample observed within 3 months of storage |
|---|---|
| 25° C. | 11 |
| 30° C. | 12 |
| 40° C. | 10 |

TABLE 2-continued

The Stability Shift of the
Creatinine Formula with Lepidine

| Storage Temperature | ND result for a 30 mg/dl sample observed within 3 months of storage |
|---|---|
| 50° C. | 11 |
| 60° C. | 10 |

As can be determined from Table 2, numerical designations (ND) of 10 to 12 were observed with a sample containing 30 mg/dL which would ideally read as 10.

While better stability was achieved with the lepidine containing formulation, there were also presented several problems. The addition of lepidine decreased the dynamic range of the test from 30 to 300 mg/dL to about 30 to 200 mg/dL. The presence of lepidine caused the creatinine formulation to turn into an occult blood test since the purpose of the lepidine is the enhance the sensitivity of the chemistry to hemoglobin. The presence of 1 mg/dL hemoglobin caused the lepidine containing formulation to read as a formulation containing 30 mg/dL creatinine as more than 300 mg/dL. This amount of interference due to hemoglobin is unacceptable for use in clinical urines which often contain blood.

The screening of other quinoline compounds similar to lepidine was carried out in order to find a derivative solving the stability problem without causing hemoglobin sensitivity and reduced dynamic range. Thirty quinoline derivatives were screened at concentrations of 25 and 100 mM. A list of the quinolines is set out in Table 3.

TABLE 3

Quinoline Derivatives Screened
in Creatinine Formulation
Quinoline Compounds Tested

| | |
|---|---|
| 8-Ethoxyquinoline sulfonic acid | 8-Nitroquinaldine |
| 2-Chloroquinoline | 6-Methylquinoline |
| 2-Chlorolepidine | 7-Methylquinoline |
| 5-Chloro-8-hydroxyquinoline | 3-Aminoquinoline |
| 2-Hydroxyquinoline | |
| 8-Hydroxyquinoline | |
| 6-Methoxyquinoline | |
| 3-Methylquinoline | |
| 8-Methylquinoline | 4-Hydroxy-2-methyl-quinoline |
| 5-Nitroquinoline | |
| 6-Nitroquinoline | 3-Bromoquinoline |
| 8-Nitroquinoline | |
| Quinaldine (2-Methylquinoline) | |
| 4-Chloro-quinaldine | 2-quinolinecarbonitrile |
| 8-Hydroxy-quinaldine | 3-quinolinecarbonitrile |

The quinolines selected for evaluation were similar to lepidine (4-methylquinoline) but with the methyl group at another position on the quinoline ring, had an amine, hydroxy or nitro group on the quinoline ring or were substituted at positions 2 or 8 since it was hypothesized that substitution at the 2 or 8 position would be effective for reduction of hemoglobin interference due to steric factors. Each quinoline derivative was incorporated into the formulation described in Example I at a concentration of 25 and 100 mM and examined for formulation compatibility (dip compatibility, impregnated paper appearance and color development); tested for hemoglobin sensitivity at 1 mg/dL hemoglobin and evaluated for its effect on thermal stability.

Of the quinolines tested, twelve were found to provide hemoglobin resistance which was better than the creatinine formula without quinoline. These quinolines were 2-Chlorolepidine, 2-Chloroquinoline, 2-Hydroxyquinoline, 8-Methylquinoline, 8-Nitroquinoline, 3-Aminoquinoline, 4-Chloroquinaldine, 5-Nitroquinoline, 6-Nitroquinoline, 4-Hydroxy-2-methylquinoline, 8-Hydroxyquinoline and 3-Bromoquinoline. Comparison of these twelve quinolines structurally supports the hypothesis that the substitution of a halogen, nitro, hydroxyl or amine group on the ring in the 2 or 8 position is the most effective means of preventing hemoglobin interference with the creatinine reagent.

Only three quinolines; 6-Methoxyquinoline, 3-Methylquinoline and 4-Hydroxy-2-methylquinoline demonstrated a stability improvement in the creatinine formulation similar to that of lepidine suggesting that a methyl in the 2, 3, 4 or 5 position or methoxy in the 2, 3, 4, 5 or 6 position is required to provide the requisite stability improvement. Two of the three quinolines, 6-Methoxyquinoline and 3-Methylquinoline gave stability and reactivity performance similar to that of lepidine. These compounds increased the overall reactivity and reduced the dynamic range of the test. The other compound, 4-Hydroxy-2-methylquinoline, did not exhibit performance similar to lepidine since it gave reactivity similar to the control with even greater resolution between levels. It was also the only quinoline compound that was found to provide hemoglobin resistance and the desired stability improvement. This quinoline is less hazardous than lepidine and is odorless. Based on the significant improvements in stability and hemoglobin resistance, 4-Hydroxy-2-methylquinoline is the preferred quinoline for use in the present invention. Quinolines substituted with amino, nitro, hydroxyl or halogen in the 2–8 position, methoxy in the 2–6 position and/or methyl in the 2–5 position would provide similar improvement due to their ability to interfere with the quinoline's ability to coordinate with hemoglobin.

The concentration of 4-Hydroxy-2-methylquinoline was varied from 50 mM to 120 mM in 10 mM increments to determine if a lower level would provide better high temperature stability. A definite relationship was observed between quinoline concentration and thermal stability with the apparent optimal quinoline concentration for this formulation being 80–110 mM. As can be determined from Table 4, numerical designations (ND) observed with samples containing 10 to 300 mg/dL creatinine were closer to the expected ND with the improved formula. The ND values observed with the quinoline additive were not affected by storage at 40° C. for 4 weeks while the ND values observed with the original formulations were affected. The analytical range of the improved formulation was also greater.

TABLE 4

Creatinine Improvement Formulation versus Original Creatinine Reagent

| Concentration Expected ND | Storage temp. | Weeks stored | 10 mg/dl 10 observed ND mean | | 50 mg/dl 20 observed ND mean | | 100 mg/dl 30 observed ND mean | | 200 mg/dl 40 observed ND mean | | 300 mg/dl 50 observed ND mean | |
|---|---|---|---|---|---|---|---|---|---|---|---|---|
| Formula | | | mean | sd | mean | sd | mean | sd | mean | sd | mean | sd |
| Original Creatinine with no quinoline | −20 C. | 2 | 7.8 | 1.4 | 9.8 | 1.9 | 20.3 | 1.3 | 29.8 | 1.6 | 40.0 | 2.8 |
| | | 4 | 7.3 | 0.5 | 12.2 | 1.6 | 23.7 | 2.4 | 32.7 | 2.3 | 43.0 | 2.3 |
| | 40 C. | 2 | 9.2 | 1.4 | 14.3 | 2.5 | 23.2 | 1.9 | 30.1 | 2.0 | 40.6 | 1.9 |
| | | 4 | 12.0 | 1.1 | 18.3 | 2.3 | 24.9 | 2.6 | 32.5 | 3.2 | 42.8 | 3.7 |
| Improved Creatinine with 4-hydroxy 2-methyl-quinoline | −20 C. | 2 | 8.1 | 1.6 | 17.3 | 2.0 | 27.2 | 2.5 | 37.9 | 2.7 | 45.5 | 2.3 |
| | | 4 | 8.5 | 1.6 | 18.7 | 1.8 | 26.3 | 2.5 | 40.6 | 3.3 | 45.3 | 2.1 |
| | 40 C. | 2 | 10.4 | 0.7 | 20.5 | 2.4 | 28.1 | 2.4 | 38.4 | 3.2 | 46.3 | 2.0 |
| | | 4 | 11.3 | 1.2 | 19.0 | 4.0 | 25.8 | 4.1 | 36.5 | 4.0 | 44.6 | 4.0 |

Interference testing was carried out with ascorbic acid and hemoglobin. Concentrations of 1 to 10 mg/dL hemoglobin and 25 to 440 mg/dL ascorbic acid were tested in a 50 mg/dL creatinine urine standard with both the improved creatinine formulation and the original creatinine reagent. Results of interference testing, using a CLINITEK®-50 reflectance spectrometer, are set out in Table 5.

are labeled with a direction not to use them on visibly bloody urine which occurs at about 5 mg/dL hemoglobin.

With regard to ascorbate resistance, the current creatinine test exhibited an 82% gain in reactivity in the presence of 25 mg/dL ascorbate. In comparison, the improved creatinine test demonstrated resistance to 25 mg/dL ascorbate and also to ascorbate at a concentration of 440 mg/dL, twenty times

TABLE 5

Hemoglobin and Ascorbate Resistance of Current and Improved Creatinine Reagents

| | | | CLINITEK ® 50 Decode Result | | | | | | | |
|---|---|---|---|---|---|---|---|---|---|---|
| | [Interferent] | Stab | <10 mg/dL | | 50 mg/dL | | | 100 mg/dL | | |
| Form. | (mg/dL) | Cond. | Mean | SD | Mean | SD | % Change | Mean | SD | |
| Original creatinine formula without quinoline | none | 2W25C | 541 | 12 | 486 | 10 | | 383 | 7 | |
| | 1 Hb | 2W25C | | | 489 | 10 | −0.3 | | | |
| | 2 Hb | 2W25C | | | 461 | 11 | 24.3 | | | |
| | 4 Hb | 2W25C | | | 415 | 8 | 68.9 | | | |
| | 6 Hb | 2W25C | | | 382 | 7 | 101.0 | | | |
| | 10 Hb | 2W25C | | | 335 | 12 | 146.6 | | | |
| | 25 AA | 2W25C | | | 395 | 12 | 88.4 | | | |
| | 440 AA | 2W25C | | | 284 | 12 | 196.1 | | | |
| Improved creatinine | none | 2W25C | 528 | 9 | 437 | 7 | | 327 | 9 | |
| | 1 Hb | 2W25C | | | 443 | 13 | −0.5 | | | |
| | 2 Hb | 2W25C | | | 427 | 6 | 9.1 | | | |
| | 4 Hb | 2W25C | | | 418 | 9 | 17.3 | | | |
| | 6 Hb | 2W25C | | | 402 | 10 | 31.8 | | | |
| | 10 Hb | 2W25C | | | 380 | 7 | 51.8 | | | |
| | 25 AA | 2W25C | | | 429 | 6 | 7.3 | | | |
| | 440 AA | 2W25C | | | 442 | 12 | −0.5 | | | |

1) Hb = hemoglobin
2) AA = ascorbate
3) Decode = a number representing the reflectance of color off the reagent as measured by the CLINITEK ® 50 instrument. The lower the number, the more color has been generated. The typical decode responses for three creatinine levels; 10, 50 and 100 mg/dL; are provided for comparison.

Referring to Table 5, the standard creatinine formulation was found to exhibit both greater hemoglobin and ascorbate sensitivity than the improved formulation of the present invention. The test, absent the quinoline of the present invention, shows a 147% increase in reactivity with 10 mg/dL hemoglobin concentration compared to 52% for the quinoline containing formulation. In general, a three fold improvement in hemoglobin resistance was observed with the improved creatinine test at all concentrations of hemoglobin tested. In actual practice, the urine sample being tested would not contain such a high concentration of hemoglobin because the devices used for this sort of assay the amount normally found in clinical urines. Thus, both hemoglobin and ascorbate resistance are significantly improved with the reagent of the present invention.

We claim:

1. An assay for creatinine in urine in which the urine is contacted with a reagent system comprising cupric ions, a hydroperoxide and an oxidizable dye together with 4-hydroxy-2-methylquinoline.

2. The assay of claim 1 wherein the 4-hydroxy-2-methylquinoline is present in the reagent system at a concentration of from 10 to 300 mM, the hydroperoxide is diisopropyl benzene dihydroperoxide and the oxidizable dye is 3,3',5,5'-tetramethylbenzidine.

3. The assay of claim 1 wherein the reagent system is dried onto a strip of absorbent material to provide a dry assay in which the strip is contacted with the urine.

4. An assay for creatinine in a urine test sample suspected of containing creatinine together with hemoglobin, ascorbate or both which assay comprises contacting the urine test sample with a reagent system containing cupric ions, a hydroperoxide and an oxidizable dye which reagent system also contains 4-hydroxy-2-methylquinoline.

5. The assay of claim 4 wherein the 4-hydroxy-2-methylquinoline is present in the reagent system at a concentration of from 10 to 300 mM, the hydroperoxide is diisopropyl benzene dihydroperoxide and the oxidizable dye is 3,3',5,5'-tetramethylbenzidine.

6. The assay of claim 4 wherein the reagent system is dried onto a strip of absorbant material to provide a dry assay in which the strip is contacted with the urine.

* * * * *